United States Patent
Flexman et al.

(10) Patent No.: US 11,553,966 B2
(45) Date of Patent: Jan. 17, 2023

(54) DEVICE VISUALIZATION THROUGH OPTICAL SHAPE SENSING OF A GUIDEWIRE

(71) Applicant: KONINKLIJKE PHILIPS N.V., Eindhoven (NL)

(72) Inventors: Molly Lara Flexman, Melrose, MA (US); Gregory Cole, Ossining, NY (US); David Paul Noonan, New York, NY (US); Neriman Nicoletta Kahya, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1117 days.

(21) Appl. No.: 15/544,925

(22) PCT Filed: Dec. 31, 2015

(86) PCT No.: PCT/IB2015/060063
§ 371 (c)(1),
(2) Date: Jul. 20, 2017

(87) PCT Pub. No.: WO2016/116796
PCT Pub. Date: Jul. 28, 2016

(65) Prior Publication Data
US 2018/0014886 A1 Jan. 18, 2018

Related U.S. Application Data

(60) Provisional application No. 62/106,267, filed on Jan. 22, 2015.

(51) Int. Cl.
*A61B 34/20* (2016.01)
*A61F 2/07* (2013.01)
(Continued)

(52) U.S. Cl.
CPC ............ *A61B 34/20* (2016.02); *A61B 5/0084* (2013.01); *A61B 5/1076* (2013.01);
(Continued)

(58) Field of Classification Search
CPC ..... A61B 34/20; A61B 5/6876; A61B 5/1076; A61B 5/0084; A61B 5/6851; A61B 90/39;
(Continued)

(56) References Cited

U.S. PATENT DOCUMENTS 6,010,449 A * 1/2000 Selmon ................ A61B 5/0084
600/104
8,676,295 B2 3/2014 Cunningham et al.
(Continued)

FOREIGN PATENT DOCUMENTS

JP 2006187633 A 7/2006
JP 2008526379 7/2008

*Primary Examiner* — Amanda Lauritzen Moher
*Assistant Examiner* — Sean V Blinder (57) ABSTRACT

A medical device deployment system includes a main body (101) and a guidewire (103) capable of being passed through the main body and including a lumen. An optical shape sensing (OSS) system (104) is configured to pass through the lumen in the guidewire. The OSS system is configured to measure shape, position or orientation of an endograft (102) relative to a blood vessel for placement of the endograft.

20 Claims, 8 Drawing Sheets

(51) Int. Cl.
    *A61F 2/95*     (2013.01)
    *A61B 5/00*     (2006.01)
    *A61B 5/107*     (2006.01)
    *A61B 90/00*     (2016.01)
    *A61F 2/06*     (2013.01)

(52) U.S. Cl.
    CPC .......... *A61B 5/6851* (2013.01); *A61B 5/6876* (2013.01); *A61B 90/39* (2016.02); *A61F 2/07* (2013.01); *A61F 2/95* (2013.01); *A61B 2034/2061* (2016.02); *A61B 2090/3966* (2016.02); *A61F 2002/065* (2013.01)

(58) Field of Classification Search
    CPC ..... A61B 2090/3966; A61B 2034/2061; A61F 2/95; A61F 2/07; A61F 2002/65
    See application file for complete search history.

(56) References Cited

U.S. PATENT DOCUMENTS

| | | |
|---|---|---|
| 8,764,683 B2 | 7/2014 | Meller et al. |
| 9,204,819 B2 | 12/2015 | Grunwald et al. |
| 2002/0045832 A1* | 4/2002 | Giller .................. A61B 1/00147 600/473 |
| 2005/0131400 A1* | 6/2005 | Hennings ................ A61B 18/24 606/15 |
| 2009/0187108 A1* | 7/2009 | Tang .................... A61B 5/0066 600/475 |
| 2013/0123896 A1 | 5/2013 | Bloss et al. |
| 2013/0158512 A1* | 6/2013 | Gutierrez ........ A61M 25/09041 604/510 |
| 2014/0121751 A1 | 5/2014 | Roeder |
| 2014/0180067 A1 | 6/2014 | Stigall et al. |
| 2014/0206988 A1 | 7/2014 | Ramachandran et al. |
| 2014/0343416 A1 | 11/2014 | Panescu |
| 2015/0099942 A1* | 4/2015 | Edouard ............... A61B 5/0075 600/301 |
| 2015/0099970 A1 | 4/2015 | Schluesselberger et al. |
| 2015/0121674 A1* | 5/2015 | Belleville ............ G02B 6/3861 29/407.1 |
| 2015/0141808 A1 | 5/2015 | Elhawary et al. |
| 2016/0066794 A1 | 3/2016 | Klinder |

* cited by examiner

DEVICE VISUALIZATION THROUGH OPTICAL SHAPE SENSING OF A GUIDEWIRE

CROSS-REFERENCE TO PRIOR APPLICATIONS

This application is the U.S. National Phase application under 35 U.S.C. § 371 of International Application Serial No. PCT/IB2015/060063, filed on Dec. 31, 2015, which claims the benefit of U.S. Application Ser. No. 62/106,267, filed on Jan. 22, 2015. These applications are hereby incorporated by reference herein.

BACKGROUND

Technical Field

This disclosure relates to medical instruments and more particularly to systems, devices and methods for medical device placement/deployment with shape sensing optical fibers integrated into a guidewire, in some instances with retrofit attachments onto the device.

Description of the Related Art

Optical shape sensing (OSS) uses light along a multicore optical fiber for device localization and navigation during surgical intervention. One principle involved makes use of distributed strain measurement in the optical fiber using characteristic Rayleigh backscatter or controlled grating patterns. The shape along the optical fiber begins at a specific point along the sensor, known as the launch point (or z=0), and the subsequent shape position and orientation are relative to that point. For meaningful clinical use, shape-sensed devices may be registered to an imaging frame of reference (such as a pre-operative CT or a live fluoroscopy image).

Endovascular aneurysm repair (EVAR) has replaced open surgery as the most common technique for the repair of abdominal aortic aneurysms (AAA). The procedure is typically carried out under x-ray fluoroscopy guidance and uses significant amounts of contrast to position and deploy the stent graft correctly. On average 50-100 mL of contrast dye is used during an EVAR procedure, which may result in acute renal failure in rare cases. The most common complication from EVAR is endoleaks resulting from an insufficient seal of the stent graft to the aorta. Endoleaks involve incorrect flow around the stent (for example, flow around the stent at the proximal or distal attachment site, flow through the graft wall, retrograde flow from the branches, etc.).

Another complication around EVAR involves ischemia of the aortic side branches (such as the colonic, renal, and pelvic arteries). This can occur due to misplacement of the stent graft such that the stent partially or completely covers one of the side vessels. This is associated with a lack of high-quality imaging technology as well as the experience of the endovascular team.

In EVAR, endografts are contained within a deployment system that is used to navigate the endograft to the correct part of the vasculature. The deployment systems tend to be relatively large and stiff endovascular devices. They typically involve a handle or set of knobs and dials at the proximal end to control the various steps around the deployment. The endograft lies within a distal part of the device and is only released once the device has been navigated to the appropriate location. In some cases, the endograft completely deploys in one step, while in other cases the endograft can be partially deployed to allow for correct positioning and orientation before the final deployment step firmly attaches the endograft to the vasculature (typically through a retaining/sealing ring).

The endograft typically requires a sufficient amount of healthy vasculature where it can land its sealing ring. If this is not possible beneath the renal arteries, then the stent will cover those arteries, and must create some alternative way of maintaining flow to those vessels. This can be done with a fenestrated endograft (e.g., a endograft with windows for the side-branches) in a procedure known as fenestrated endovascular aneurysm repair (FEVAR). In this case, the endograft has fenestrations that must be lined up correctly with the side branches and additional stents are placed to connect the side vessels to the main stent.

Under x-ray guidance the endograft can be visualized through x-ray visible markers that are located in key positions on the stent. In a fenestrated stent, the markers identify the locations of the fenestrations and can be used to orient the endograft to appropriately align the fenestrations with the side vessels. Complications from EVAR includes misplacement of the endograft resulting in endoleaks, misplacement of the endograft resulting in occlusion of the side branches, contrast nephropathy due to high levels of contrast used during endograft deployment and high contrast and radiation dose due to long procedure times due to navigation and deployment in a complex anatomy. In addition, placement of a three-dimensional endograft within a three-dimensional anatomy is challenging and is typically performed under two-dimensional imaging guidance through x-ray fluoroscopy.

SUMMARY

In accordance with the present principles, a medical device deployment system includes a main body and a guidewire capable of being passed through the main body and including a lumen. An optical shape sensing (OSS) system is configured to pass through the lumen in the guidewire. The OSS system is configured to measure at least one of shape, position or orientation of an endograft relative to a blood vessel for placement of the endograft.

An endograft deployment system includes a workstation including a processor and memory. An optical shape sensing module is stored in memory and configured to interpret optical shape sensing data. A deployment system includes a tube. A guidewire is capable of being passed through the tube, and the guidewire includes a lumen. An optical shape sensing (OSS) system is configured to pass through the lumen in the guidewire. The OSS system is configured to measure at least one of shape, position or orientation of an endograft relative to a blood vessel for placement of the endograft. A registration module is configured to register the optical shape sensing data to pre-operative or intra-operative images.

A medical device deployment system includes a main body having a control handle coupled to the main body. An optical shape sensing (OSS) system is configured to measure at least one of shape, position or orientation of an endograft relative to a blood vessel for placement of the endograft. At least one clip-on attachment is configured to attach the OSS system to the control handle.

A method for endograft deployment includes deploying a guide wire having an optical shape sensing (OSS) system within a lumen of the guide wire, the guide wire configured to deliver an endograft into a vessel; measuring at least one of shape, position or orientation of the guide wire using the OSS system to identify a shape, position or orientation of the endograft during deployment; registering OSS data with image data on the vessel where the endograft is placed; anchoring the endograft in the blood vessel; and removing the guidewire and the OSS system from the vessel.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

In accordance with the present principles, a three-dimensional visualization of a stent (endograft) with respect to anatomic imaging (e.g., a pre-operative computed tomography (CT) image, an intra-operative xperCT/3DRA, a fluoroscopy roadmap, etc.) can be more accurately controlled during deployment using optical shape sensing (OSS). Introducing OSS for navigation to endovascular aneurysm repair (EVAR) can reduce radiation dose and provide a more intuitive way to position catheters and guidewires within a three-dimensional vasculature to reduce procedure times and improve outcomes.

One feature of EVAR procedures is the deployment of an endograft. The orientation and position of the endograft is an important consideration in making a good seal with the vessel and adjusting the flow such that an aneurysm is no longer under pressure. If the endograft is not positioned correctly, blood may leak around the endograft and continue to pool in an aneurysm sac, or the endograft could occlude side-vessels off the aorta which can cause poor blood flow to critical organs. In fenestrated endovascular aneurysm repair (FEVAR), side-branches (such as the renal arteries) need to be cannulated. This cannulation involves navigating a catheter and guidewire through a semi-deployed stent graft, exiting the endograft via a fenestration, and then entering the target vessel. While this can be done largely through the known position and shape of the devices through OSS, it may also be advantageous to see the position of the endograft (and corresponding fenestrations). Thus, by shape sensing the endograft, the endograft position/orientation/shape can be tracked during deployment for optimal positioning, and cannulation of side-vessels can be performed without (or with minimal) use of x-ray guidance. In one embodiment, guidance can be performed based on OSS-enabled devices, an OSS-enabled stent graft, and a pre-operative CT/live fluoroscopy.

OSS-enabled devices, such as, e.g., guidewires, catheters etc. provide an operator with knowledge of the shape and deformation and position of points on the device(s) or the entire device(s). The present principles integrate removable optical shape sensed devices into the endograft, stent, balloon, etc. prior to introduction to the body to provide enhanced visualization information during placement. To further provide the operator with knowledge of a deployable device shape, position, and orientation, OSS guidance may be introduced into the deployment process. A deployable or deployment device may include an endograft, stent, guidewire, catheter, balloon catheter, mitral clip, mitral valve, left atrial appendage (LAA) closure device, etc.

To introduce the use of OSS into an interventional procedure, the fiber needs to be integrated in the device used for the intervention. Incorporating a shape sensing fiber directly into the deployment device may call for the modification of an existing device. One solution includes an optical shape sensing fiber that is integrated into a guidewire used as a 'delivery rail' for the stent deployment system. This guidewire is then registered to the stent or endograft, and then used to model the stent or endograft position and orientation during deployment. Since the deployment device runs over the guidewire, information about the position and orientation of the device can be obtained; however, information about its state of deployment may not be available. Clipping an OSS enabled retrofit attachment onto the handle of the deployment device can be employed to provide additional information about the state of deployment and thus be used to create a more complete model of the stent or endograft position during deployment. These processes can be complemented through the use of fluoroscopy to update the model.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk read only memory (CD-ROM), compact disk read/write (CD-R/W), Blu-Ray™ and DVD.

Figure 1:
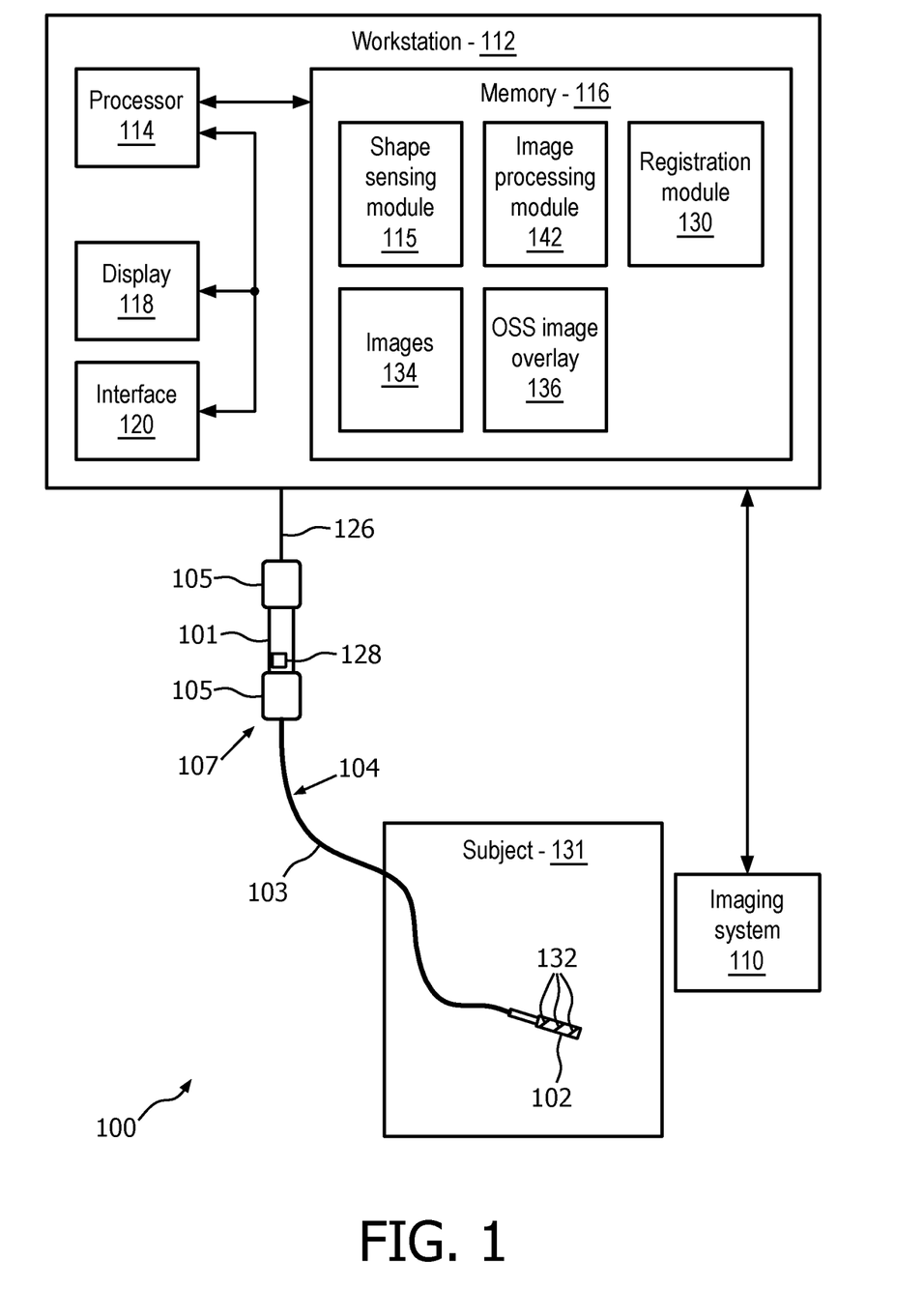
FIG. 1 is a block/flow diagram showing a system configured for endograft placement/deployment using an optical shape sensing system within a guidewire in accordance with one embodiment.

Referring now to the drawings in which like numerals represent the same or similar elements and initially to FIG. 1, a system 100 for tracking and navigation of endografts and related accessories or tools with shape sensing enabled devices and systems is illustratively shown in accordance with one embodiment. The navigation may be manually or robotically performed. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from one or more shape sensing devices or systems 104 (in FIG. 1, the OSS system 104 is located within guidewire 103, see also FIG. 2). Optical sensing module 115 is configured to use the optical signal feedback (and any other feedback, e.g., electromagnetic (EM) tracking) to reconstruct deformations, deflections and other changes associated with a medical device or instrument, such as an endograft 102 (also referred to herein as a stent graft or stent), one or more guidewires 103 (e.g., a stiff guidewire) which is passed through a deployment device or system 107, e.g., a commercially available stent deployment system. The deployment system 107 may include a tube or main body 101 through which the guidewire 103 is passed. (See, e.g., cross-section in FIG. 2). The deployment system 107 may include one or more control or stabilizing handles 105 that are employed, depending on the design to perform a plurality of tasks, e.g., to retract a sheath that supports the endograft 102, to advance a delivery device carrying the endograft 102, to adjust the guidewire 103 or any other useful function depending on the design of the deployment system 107 and the functions its needs to carry out.

The shape sensing system 104 includes one or more optical fibers 126 which are included in the system 104 in a set pattern or patterns. The optical fibers 126 connect to the workstation 112. The shape sensing system 104 may be included in a lumen of the guidewire 103 and/or other medical components involved in the procedure. The OSS fibers 126 or OSS systems 104 are employed to provide a visual representation of the deployable device, such as an endograft or stent. The present principles apply to any use of an optical shape sensing fiber 126 for navigation and deployment of the endograft 102, or deployment system 107. While described in terms of the endograft 102, the present principles can also apply to balloon catheters, clips, valves, and other implantables.

In one embodiment, the fibers 126 of the OSS system 104 are integrated within or through the guidewire 103, the deployment system 107 and/or the handle 105 of the deployment system 107. The OSS system 104 can be employed for making physical measurements. The measurements may be employed for planning or for placement of the endograft 102. The endograft 102 may also include an OSS system 104 to provide position and orientation information for the endograft 102 itself.

Shape sensing system 104 with fiber optics may be based on fiber optic Bragg grating sensors in one or more optical fibers. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, strain causes a shift in the Bragg wavelength.

One advantage of this technique is that various sensor elements can be distributed over the length of a fiber.

Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

It should be understood that optical shape sensing may be performed in a plurality of ways and is not limited to FBGs or Rayleigh scatter techniques. For example, other techniques may include channels etched into the fiber, employing quantum dots for reflection, employing a plurality of separate fibers (e.g., 3 or more) instead of a single multicore fiber or other optical shape sensing techniques.

Workstation 112 includes a display 118 for viewing internal images of a subject (patient) or volume 131 and may include an image 134 (preoperative or intraoperative images) or an image 136 (OSS data) as an overlay or other rendering registered with the shape sensing system 104 in one or more of the components employed in the procedure. Display 118 may also permit a user to interact with the workstation 112 and its components and functions (e.g., touchscreen, graphical user interface, etc.), or any other element within the system 100. This is further facilitated by an interface 120 which may include a keyboard, mouse, a joystick, a haptic device, or any other peripheral or control to permit user feedback from and interaction with the workstation 112.

In one embodiment, an OSS fiber 126 or OSS system 104 or OSS enabled device 103, 105, 107, etc. is coupled to the endograft 102. The OSS fiber 126, OSS system 104, etc. is/are registered to a feature or features of the endograft 102.

By integrating an OSS enabled device 103, 105 107, OSS fiber 126 or OSS system 104, geometric information about the graft 102 may be collected and ultimately used to visualize the graft 102.

A registration module 130 is configured to register the OSS fiber 126 or system 104 to a physical structure (e.g., aneurysm, etc.), other OSS systems 104, images 134, 136, the guidewire 103, the handle 105, the endograft 102, etc. For shape recognition registration, a distinctive shape or shape template 128 can be employed to obtain both position and orientation information from the fiber 126. If the fiber 126 takes a predefined and immutable path, the curvature and shape information of that path can be used to identify a unique image to fiber transformation to be stored in memory 116.

An image processing module 142 is configured to combine images (134) and OSS position data (image 136) for joint or separate display on the display 118. The OSS data 136 and the image data (from pre-operative or intraoperative images 134) can be registered and jointly displayed to assist in placement of the endograft 102 (or other stent or implantable device). An imaging system 110 may include a fluoroscopy system (x-rays) for collecting real-time visual information about positions of instruments or anatomical features. Images 134 collected with the imaging device 110 may be registered with the OSS data from OSS system 104.

One step in endograft 102 deployment is the positioning of x-ray visible (radiopaque) markers 132. These are initially positioned when the endograft 102 is advanced on the guidewire 103 to the approximate location. If the endograft can be semi-deployed (as in FEVAR), then the markers 132 are re-used to fine tune the position of the endograft 102. Placement of a three-dimensional endograft 102 within a three-dimensional anatomy is challenging and is typically performed under two-dimensional imaging guidance through x-ray fluoroscopy. As a consequence, misplacement of the endograft 102 can occur, and procedure times can become very long.

During a conventional FEVAR procedure, a significant portion of time is spent cannulating the fenestrations of an endograft to ensure alignment with an underlying vasculature. Specifically, the operator attempts to align all fenestrations, or windows, to ensure side branches are not occluded by the main stent graft body. The operator must navigate up and into the main stent graft body, then exit the fenestration and enter the side vessel. To do this, the anatomy needs to be seen as well as the position and orientation of the endograft.

By shape sensing a guidewire 103 and/or a portion of the deployment system 107, e.g., the handle 105, and thus the position of the endograft (or at least the relevant markers on the endograft), the navigation can be simplified. Then, navigation can be performed using the registered pre-operative (e.g., CT) images for guidance. To introduce the use of optical shape sensing into an interventional procedure, it is first necessary to integrate the fiber into one or more of the devices/systems used for the intervention. Given the complexity of these systems, such integration would be both technically challenging and would require significant changes to existing designs. However, by integrating optical shape sensing into the guidewire 103 used during endograft deployment and registering the endograft 102 to the guidewire 103 in accordance with the present principles, the system 100 can be used with any type of stent and/or deployment system 107 with limited impact on design of the endograft or the deployment mechanism.

In accordance with particularly useful embodiments, the OSS system 104 is integrated into the guidewire 103 over which the endograft deployment system 107 is placed. The deployment system handle 105 is coupled to the guidewire 103 and any motion of the endograft 102 is tracked with respect to the guidewire 103. The endograft 102 is registered to the OSS system 104 in the guidewire 103. The guidewire 103 may include a stiff guidewire having diameter of between about 0.014 to about 0.045 inches, and typically about 0.035 inches.

While the present principles may be applied to any interventional guidewire used in combination with a stent or endograft, the present embodiments employ the guidewire 103 with a lumen or channel therein for OSS system 104 to be disposed so that the position and orientation of the guidewire 103 is known. Such a guidewire 103 acts as a 'delivery rail' for the stent deployment tool (107), which passes down a dedicated guidewire lumen within the deployment system 107. Since the guidewire 103 is physically inside the deployment system 107, the reconstructed shape of the guidewire 103 is representative of the shape of the deployment system 107. However, the guidewire 103 is free to rotate and translate inside the deployment system 107, and therefore, the precise position and orientation of the endograft 102, x-ray visible markers 132 or the tip of the deployment system 107 may be unknown.

The configuration of the deployment system 107 is such that one handle 105 may be connected to the endograft 102 in an axially and torsionally stiff manner. This permits re-orientation of the endograft 102 intra-operatively but can also be re-purposed to maintain a registration between the guidewire 103 and the deployment system 107. This can be achieved in several different ways.

Figure 2:
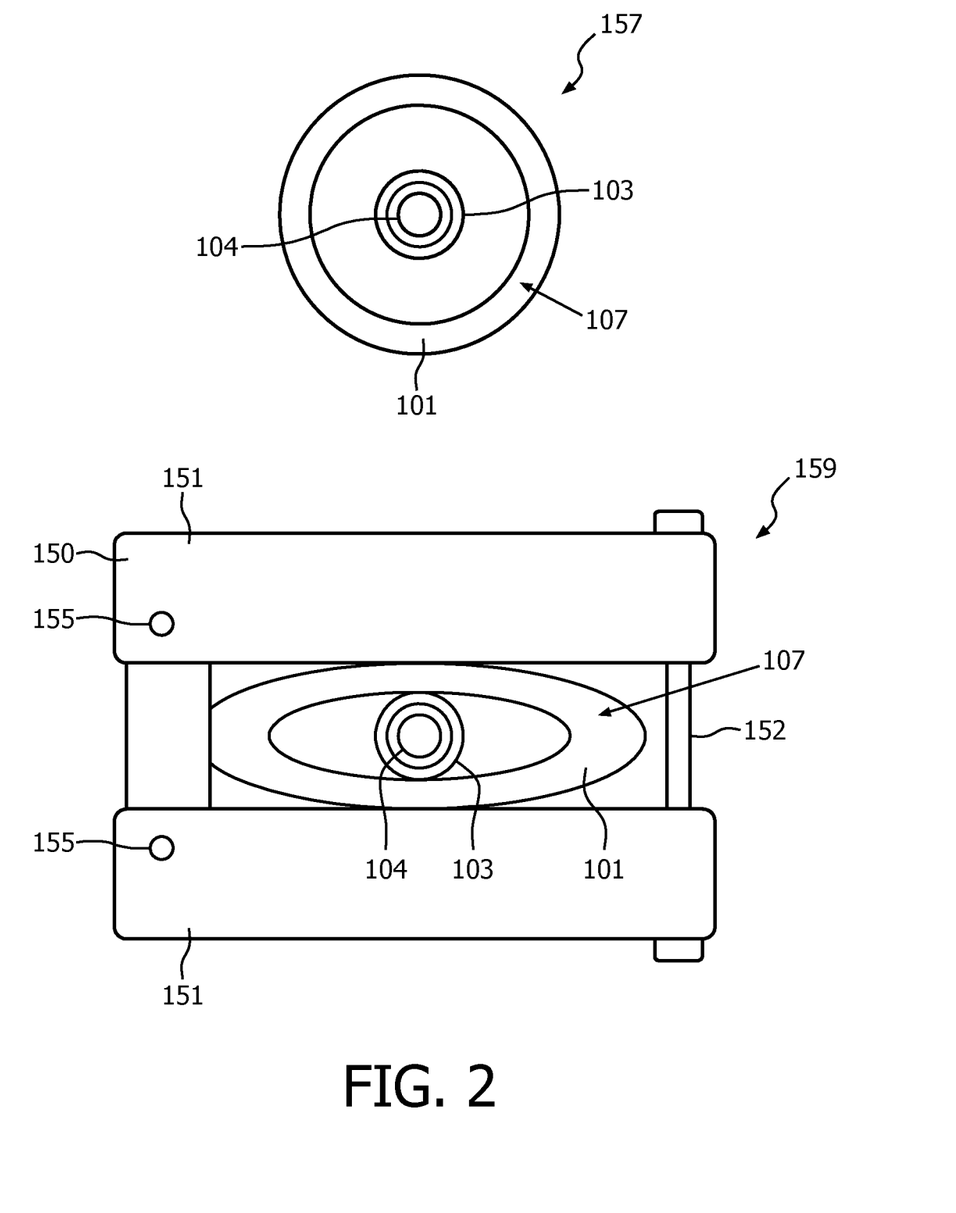
FIG. 2 is a diagram showing a cross-section of an unclamped and a clamped assembly having an OSS system, guidewire and tube of a deployment system in accordance with one embodiment.

Referring to FIG. 2, in one embodiment, a clamping mechanism 150 is employed between the guidewire 103 and the deployment system 107. In cross-sectional view 157, the guidewire 103 and the deployment system 107 are shown unconstrained. In cross-sectional view 159, the guidewire 103 and the deployment system 107 are illustratively shown constrained by the clamping mechanism 150. In this embodiment, the deployment system 107 is advanced over the guidewire 103 until positioned at an approximately correct desired insertion depth. Once at this location, the clamping mechanism 150 within the deployment system 107 would be activated thus physically coupling the deployment system 107 to the guidewire 103. Thus, pending registration between the OSS system 104 and a known feature in the deployment system 107 (such as x-ray visible markers), any subsequent manipulation of the deployment system 107 is known with respect to a shape sensing co-ordinate system.

The clamping system 150 may include a system that is integrated into the handle 105 of the deployment device 107 or a retrofit system that attaches to the deployment system 107 and then clamps the guidewire 103 proximal to entry into the deployment system 107. The clamping mechanism 150 includes a release 152 to permit clamping and reclamping of the guidewire 103 so that there is still the ability to freely manipulate the guidewire 103. Alternately, the release 152 may include an actuated release so that the user does not have to apply the clamping force by hand.

The clamping mechanism 150 may include chucks 151 that compress a tube 101 of the deployment system 107. The chucks may be hingedly connected and employ one or more pivot axes 155. The clamping mechanism 150 may be placed at an entry point of the guidewire to the deployment system 107, although it may also be placed at other locations, e.g., at a point distal to the handle 105 (such as at the tip of the deployment system 107, within a spindle of the deployment system, or at the proximal position of a loaded stent). Multiple clamping points along the deployment system 107 (such as proximal and distal to the deployment system 107) may be employed. The OSS system 104 may be fixed within the guidewire lumen at the point of the clamping. This may include a temporary or permanent fixation point.

It should be understood that the clamping mechanism 150 is merely illustrative of one technique for fastening the guidewire 103 to the deployment system 107 other mechanisms, such as grips, pins, brakes, etc. may also be employed in accordance with the present principles.

Figure 3:
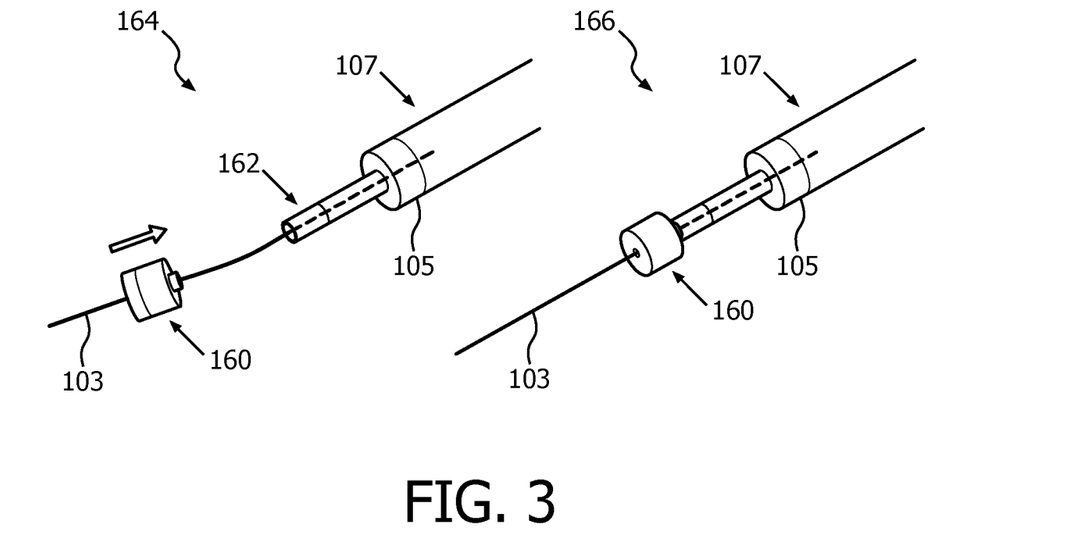
FIG. 3 is a diagram showing a guidewire coupling mechanism prior to and after engagement with a deployment system in accordance with one embodiment.

Referring to FIG. 3, a coupling feature 160 may be placed on the guidewire 103 and deployment system 107. In one embodiment, the guidewire 103 has a predefined coupling feature 160 at a certain location along its length. This could be an adjustable torquer or a more permanent feature bonded to the guidewire 103 at a fixed location. The deployment system 107 also has a coupling feature 162 at the proximal end of the handle 105 such that when both mating features come in contact they engage and rigidly connect the two devices together. Alternatively, the guidewire 103 may clamp onto the handle 105 of the deployment system 107 with no modification to the device handle 105.

Where the coupling feature 160 is rigidly fixed to the guidewire 103, the fixed location could be such that the tip of the guidewire 103 aligns with the tip of the deployment system 107 when the mating components are coupled together, or at any other pre-defined position within or outside the device lumen (103). Defining the positioning of this fixed location with respect to the endograft 102 may be part of a pre-registration protocol. In a further embodiment, the coupling of the two devices could take place at the distal tip of the deployment system 107. View 164 shows the coupling features 160 and 162 prior to engagement, and view 166 shows the coupling features 160 and 162 after engagement.

Figure 4:
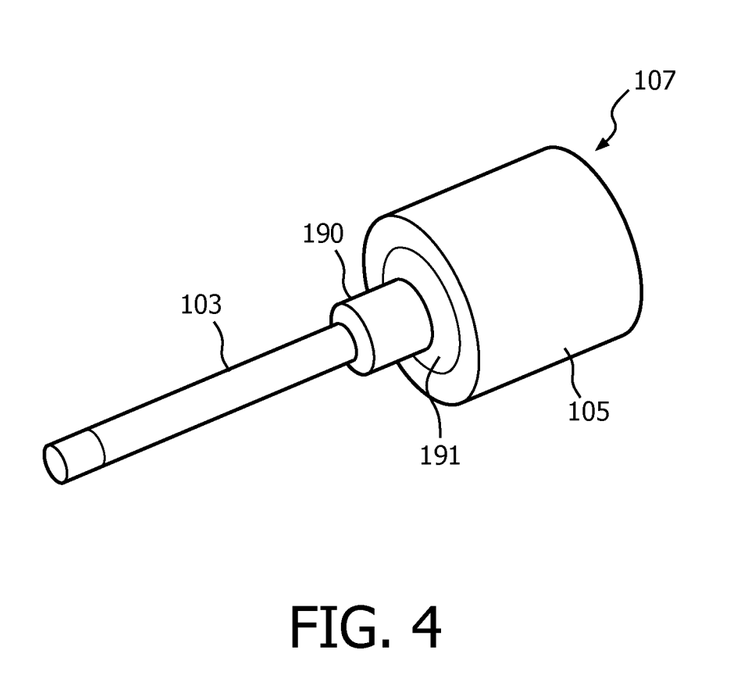
FIG. 4 is a perspective view showing a rotational sensor assembly between a guidewire and a handle of a deployment system in accordance with one embodiment.

Referring to FIG. 4, another embodiment includes a rotational tracking sensor 190 that tracks rotation between the handle 105 and the guidewire 103. In cases in which it is not desirable to have the guidewire 103 rotationally coupled to the deployment system 107, it is possible to incorporate sensors 190 into the handle 105 or attachment piece such that the guidewire 103 connects to the deployment system 107 in a manner which enables the relative rotation and translation of the two devices to be measured. This embodiment may include an optical encoder (190) (or similar mechanism) within the handle 105 to measure rotation, and a linear potentiometer 191 (or similar mechanism) embedded within the handle 105 but which couples to the guidewire 103.

Figure 5:
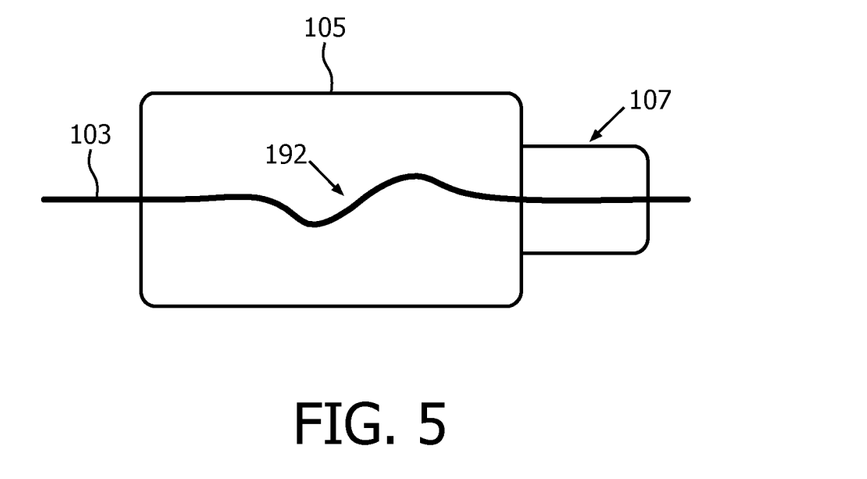
FIG. 5 is a side cross-sectional view showing a shape template for a guidewire within a handle of a deployment system in accordance with one embodiment.

Referring to FIG. 5, another embodiment tracks the handle 105 and the guidewire 103 using a template 192 with the OSS system 104, using a known shape in the template 192 within the guidewire lumen. If the guidewire 103 is forced to pass through a specific shape within the handle of the deployment system 107, its position and orientation with respect to the system can be identified.

Figure 6:
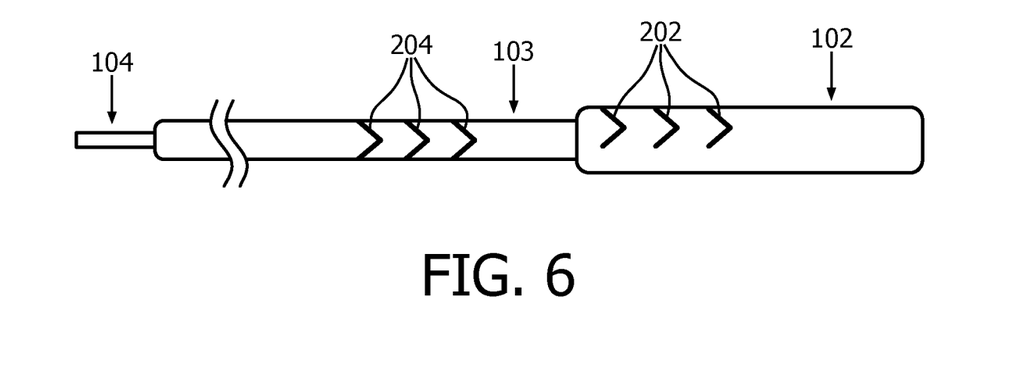
FIG. 6 is a side view showing a guidewire and an endograft with radiopaque registration markers in accordance with one embodiment.

Referring to FIG. 6, the endograft 102 may be registered to the guidewire 103 in a number of ways. These may include registering the OSS system 104 in the guidewire 103 to x-ray visible markers 202 on the stent or endograft 102. This can be performed using an x-ray registration that employs a tip of the guidewire 103 and the markers 202 visible in the x-ray image to determine their relationship. In some cases, the tip of the guidewire 103 may not be visible within the same x-ray image as the stent 102. An alternative way to perform this registration is to make unique x-ray visible bands 204 on the guidewire 103 along its distal length so that one of those bands is likely to be in close proximity to the endograft or stent 102, and thus enable registration. Additional methods of registering the OSS system 104 are also contemplated.

By registering the position of the markers 202 to the guidewire 103 or to markers 204 on the guidewire 103, a virtual representation of the markers 202, 204 can be displayed within the 3D visualization framework (e.g., on display 118, FIG. 1). Then, as the deployment system 107 is manipulated, the position of the markers 202, 204 can be updated accordingly. Similarly a 3D model of the stent graft 102 can be deformed according to the known positions of the markers 202, 204 and the OSS shape data from OSS system 104.

A 2D overlay of a fluoro image of the stent 102 can be displayed to the user and adapted based on the guidewire position and orientation. This is particularly useful, for example, in FEVAR when the main body stent has been partially deployed and navigation is underway to cannulate the side vessels using OSS-enabled devices. In this situation, knowing the position of the fenestration markers 202 on the stent 102 can provide additional information for navigating through the stent 102 and into side vessels. The stent 102 can be visualized using the information provided by tracking the guidewire 103.

It should be noted that in the case of a semi-deployable stent, once the initial position of the stent 102 has been identified and the stent 102 semi-deployed, registration needs to be repeated prior to any further navigation of other OSS enabled devices (catheters guidewires, etc.) through the fenestrations, etc. This is due to the fact that the stent graft 102 will expand and the position of the x-ray visible markers 202 will shift.

A virtual representation of the stent graft as a full 3D model of the stent may be employed in various stages of deployment. Such a representation would clearly provide a further simplified navigation task. Especially in the case of stenting, where it is important to carefully maintain mechanical properties, it may be preferable to not interfere with the functional properties of the endograft 102. In addition, there are typically many types of endograft 102 that use only one type of deployment handle 105. An OSS system 104 may be employed as a retrofit attachment onto the handle. In this way, multiple stents can be addressed by one design.

Figure 7:
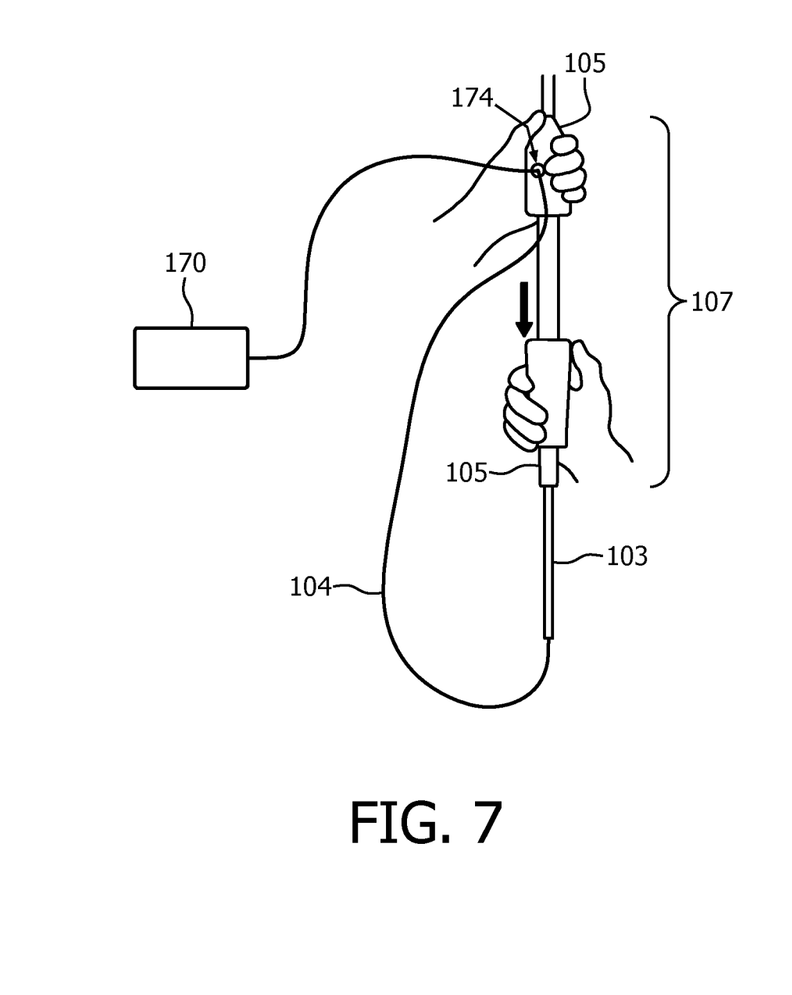
FIG. 7 is a diagram showing an OSS system for a guidewire coupled to a handle of a deployment system in accordance with one embodiment.

Referring to FIG. 7, another embodiment tracks the handle 105 and the guidewire 103 using a same OSS system 104. A proximal end of the OSS system 104 exits the guidewire 103 and is connected to a fixed point (attachment point) 174 on the deployment system 107 before returning to a launch fixture 170. As before, the location of this fixed point 174 is preferably on the distal handle 105 of the deployment system 107 since this rigidly coupled to a main backbone of the system 107 and thus the location of the endograft 102.

Figure 8:
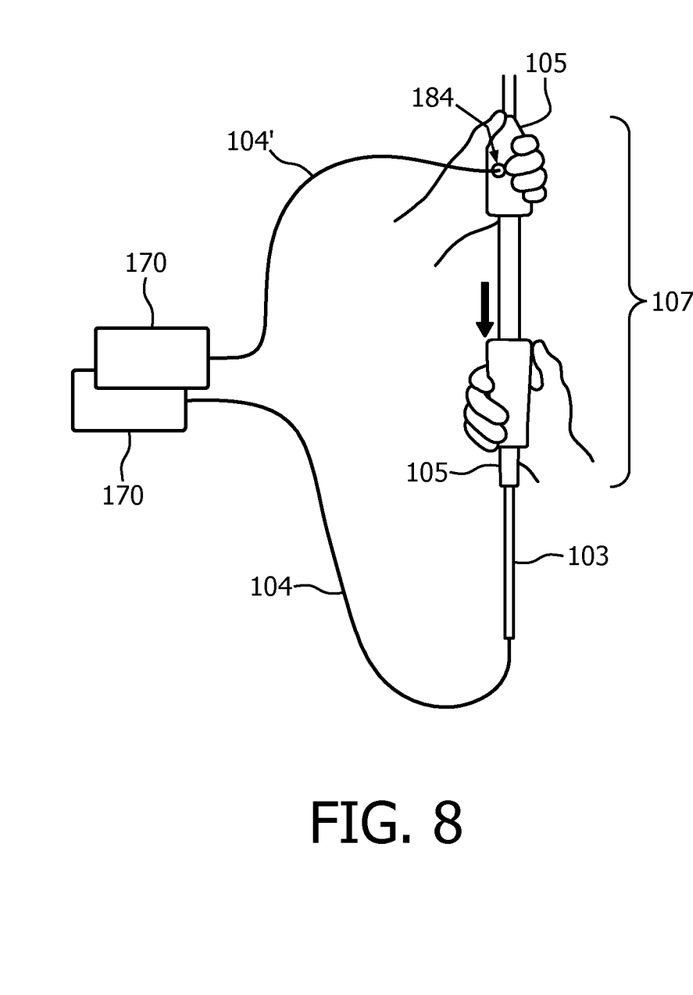
FIG. 8 is a diagram showing an OSS system for a guidewire and an additional OSS system coupled to a handle of a deployment system in accordance with another embodiment.

Referring to FIG. 8, another embodiment tracks the handle 105 and the guidewire 103 using different OSS systems 104. A second OSS system 104' is attached to a fixed point 184 on the deployment system 107 and registered to a shape sensing co-ordinate system. The location of this fixed point 184 is preferably at a point on the handle 105 of the deployment system 107 since this is rigidly coupled to a main backbone of the system 107 and thus the location of the endograft 102. This configuration permits the guidewire 103 to be rotated and translated with respect to the deployment system 107.

Figure 9:
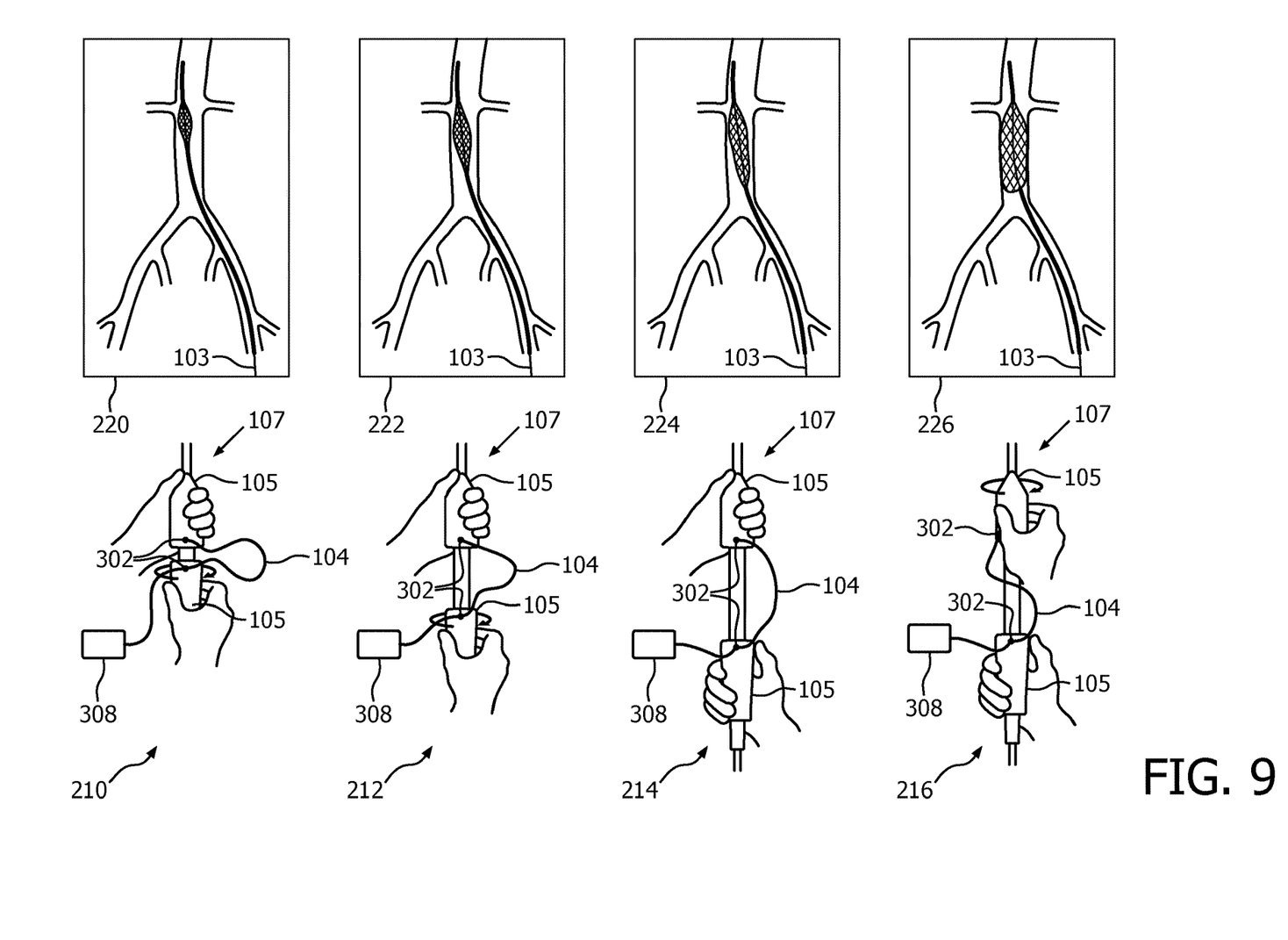
FIG. 9 is a diagram showing relative positions of handles of a deployment system measured by an OSS system and corresponding model displays showing the relative effects in accordance with one embodiment.

Referring to FIG. 9, four positions 210, 212, 214 and 216 of a deployment system are depicted with corresponding model images 220, 222, 224 and 226 of blood vessels having a stent 102 being deployed therein, are depicted. A clip-on attachment 302 (or set of attachments) may be included to connect one or more OSS systems 104 to a handle or handles 105 of the deployment system 107. A method for registering the stent 102 to the OSS system 104 is also needed. The clip-on attachment 302 that connects to the deployment system 107 can provide a simple way to enable visualization of the endograft deployment process. Motions at a proximal portion of the deployment system 107 directly map to changes in the stent position and state of deployment.

In one embodiment, the clip-on attachment 302 includes adhesive strips or pieces that are employed that attach to the OSS system 104 and are fixed to the proximal and distal handles 105 of the deployment system 107. The OSS system 104 returns back to a launch base or fixture 308 where its origin resides. Clips 302 can be removed and re-applied for another stent deployment within a same procedure. The clips 302 can be comprised of a mechanical fixation device (e.g., clip, toggle clamp, spring clasp, etc.), an adhesive, a magnetic attachment, a band or other attachment device.

The position of the stent graft 102, the orientation of the stent graft 102 and the state of deployment (how many of the individual stents on the stent graft have been deployed) need to be known. There are three primary features that need be known about the stent to provide a meaningful visualization. It is assumed that a shape sensed guidewire 103 is being used as part of the deployment process. This guidewire 103 can provide part of the information to determine the position of the stent 102. In some cases, the guidewire 103 may not be coupled to the deployment system 107 so it does not provide information about the orientation. The clip-on attachment 302 can sense the orientation of a retaining ring of the stent graft 102 (or whichever portion of the stent graft that is rigidly attached to the deployment system 107) because the orientation of the distal portion of the handle 105 is directly coupled to the orientation of the attachment site of the stent graft 102 (very stiff torsionally). This is what enables the fine manipulation of the stent graft 102 during deployment. Therefore, by sensing the position of the distal deployment handle 105, the orientation of the attachment point on the stent graft 102 can be extracted.

The clip-on attachment 302 may provide information about the state of deployment of the stent graft 102 by measuring a relative position of actuating elements (e.g., handles 105) of the stent deployment system 107. As shown in FIG. 9, separation between the distal and proximal handles 105 on the deployment system directly relates to how many individual stents or stent length that has been released. Visualization of the stent deployment using shape sensing on the handles 105 with a clip-on attachment 302 includes OSS system 104 attached to both distal and proximal handles.

It would also be possible to infer the state of stent deployment by incorporating the OSS system 104 into the handle or handles 105 of the deployment system 107 without modification of the multiple different deployment systems available on the market. Interfacing of the OSS system(s) 104 can be done with a separate OSS visualization framework. The clip-on attachment 302 provides the same functionality as the embodiments described above without the need for handle modifications. The clip-on attachment 302 to the handle 105 can be done with a different OSS system 104 than that employed for the guidewire 103, or by using the OSS system 104 after leaving from a proximal portion of the guidewire 103.

Figure 10:
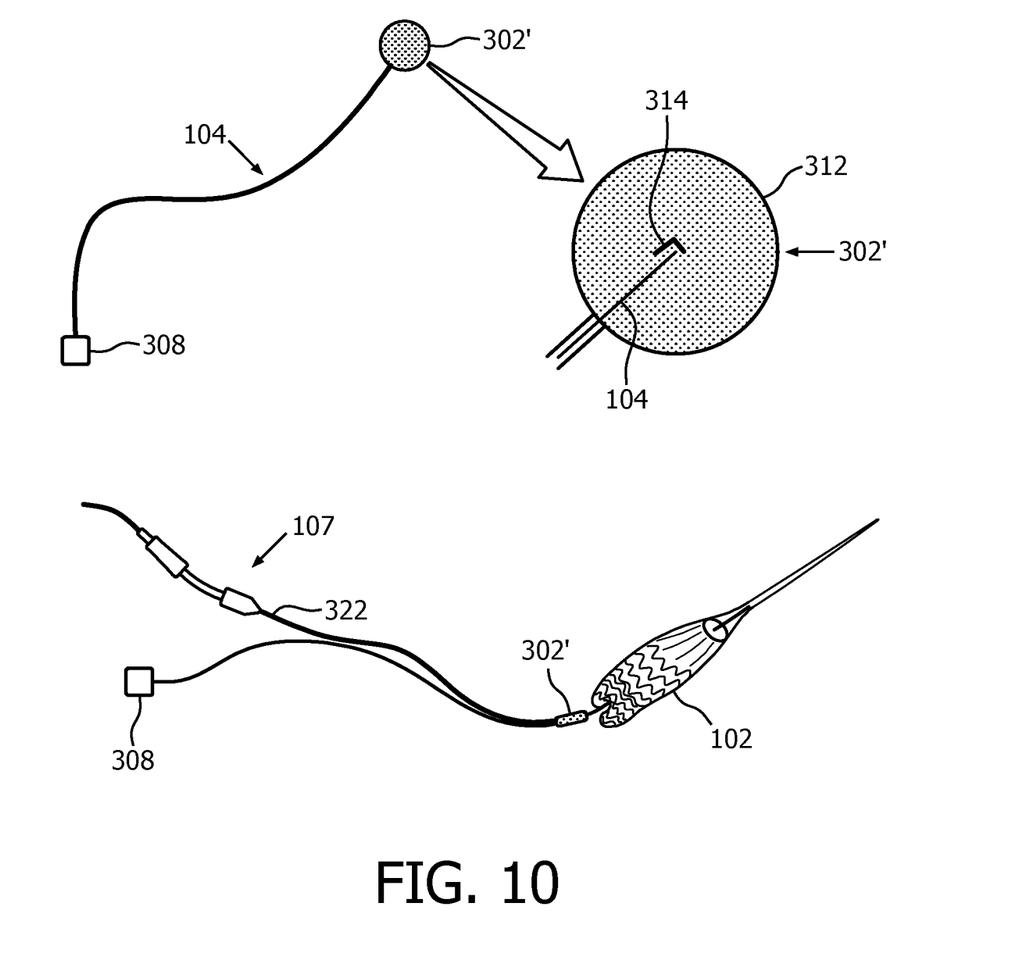
FIG. 10 is a perspective view showing a clip-on attachment mechanism coupled to a deployment system and a magnified view of an OSS system with the clip-on attachment mechanism in accordance with one embodiment.

Referring to FIG. 10, an illustrative deployment system 107 is shown along with a magnified view of an adhesive clip-on attachment 302'. In addition to attaching onto the handle 105, the adhesive or clip attachment 302' can also be used to sense a distal portion of the deployment system 107. This clip 302' may include an adhesive attachment or patch 312 that couples the OSS system 104 to the outside of the deployment system 107. This adhesive patch 312 can also have a radiopaque marker 314 integrated into it for registration purposes. The OSS system 104 travels back from the deployment system 107 to a launch fixture 308 outside the body. Alternatively, it could travel back to an attachment point on the handle 105.

Once the clip-on attachment 302, 302' has been fixed to the deployment system 107, it may not be necessary to register the endograft 102 to the deployment system 107 if the stent 102 is incorporated into the deployment system 107 in the same way each time for a given stent deployment product. However, it is likely that it will be necessary to register each stent to the deployment system 107 prior to use.

There is a very torsionally stiff relationship between the stent anchor (e.g., anchor ring) and the handle 105, which is what gives the handle 105 the ability to re-orient the stent 102 during deployment. The more important registration is in orientation. This relationship will likely vary in each stent 102. For this reason, the Information for Use (IFU) for each stent 102 includes a step at the beginning of the process where the stent 102 is visualized under x-ray by the operator, rotated based on the x-ray visible markers (202) present, and then mentally mapped to an indicator 322 on the handle 105 so as to remember an 'optimal' orientation for deployment. After navigating, the operator then returns the handle 105 to the optimal orientation (as indicated by a recalled position of the dot 322). This same procedure can be used following attachment of the OSS system 104. For example, the stent 102 is rotated until it is fully in plane (based on the marker bands 202) and then that position is used to map the OSS system 104 to the stent 102 in orientation. This could be done manually or rob optically.

The next important registration is in position. This is principally the distance along the deployment system 107 between the stent 102 and the OSS clip 302 onto the handle 105. Specifically, the position of the x-ray visible markers (202) within the stent 102 should be known. This distance can be identified using a multitude of different methods. For example, one embodiment would include a priori knowledge of the mechanical construction of the stent deployment system 107. Another embodiment includes determining the distance under x-ray guidance. If the shape sensing base is registered to the x-ray system then the stent deployment system 107 can be placed straight and with the stent visible under x-ray. The marker bands (204) can be selected in the image and then the distance between the clips (302) on the handle (105) and the marker bands will be known. This can be done prior to deployment as the marker bands are visible at that time. Another embodiment employs an x-ray image of the stent deployment system 107 that can be used to identify the offset between the deployment system tip and the marker bands (204) on the stent graft 102. From the known orientation, position, and state of deployment, a model of the endograft can be generated and displayed to the user.

The present principles can be applied to any use of an optical shape sensing fiber or system for navigation and deployment of a stent, stent-graft, or stent deployment system. The present principles can also be applied to any stent and balloon, i.e., to any over the wire therapy device, to track the position of the device in the vessel, to help position the device and deliver therapy with less x-ray and less contrast media volume. In such embodiments, a stiff guidewire would likely be replaced by a more flexible wire, either or both may be OSS tracked.

It should be understood that the present principles cover any of the applications where an endograft is deployed under fluoroscopic or other guidance including, but not limited to procedures, such as, e.g., endovascular aneurysm repair (EVAR), branch-fenestrated EVAR (BEVAR), percutaneous EVAR (PEVAR), thoracic EVAR (TEVAR), fenestrated EVAR (FEVAR), etc.

Figure 11:
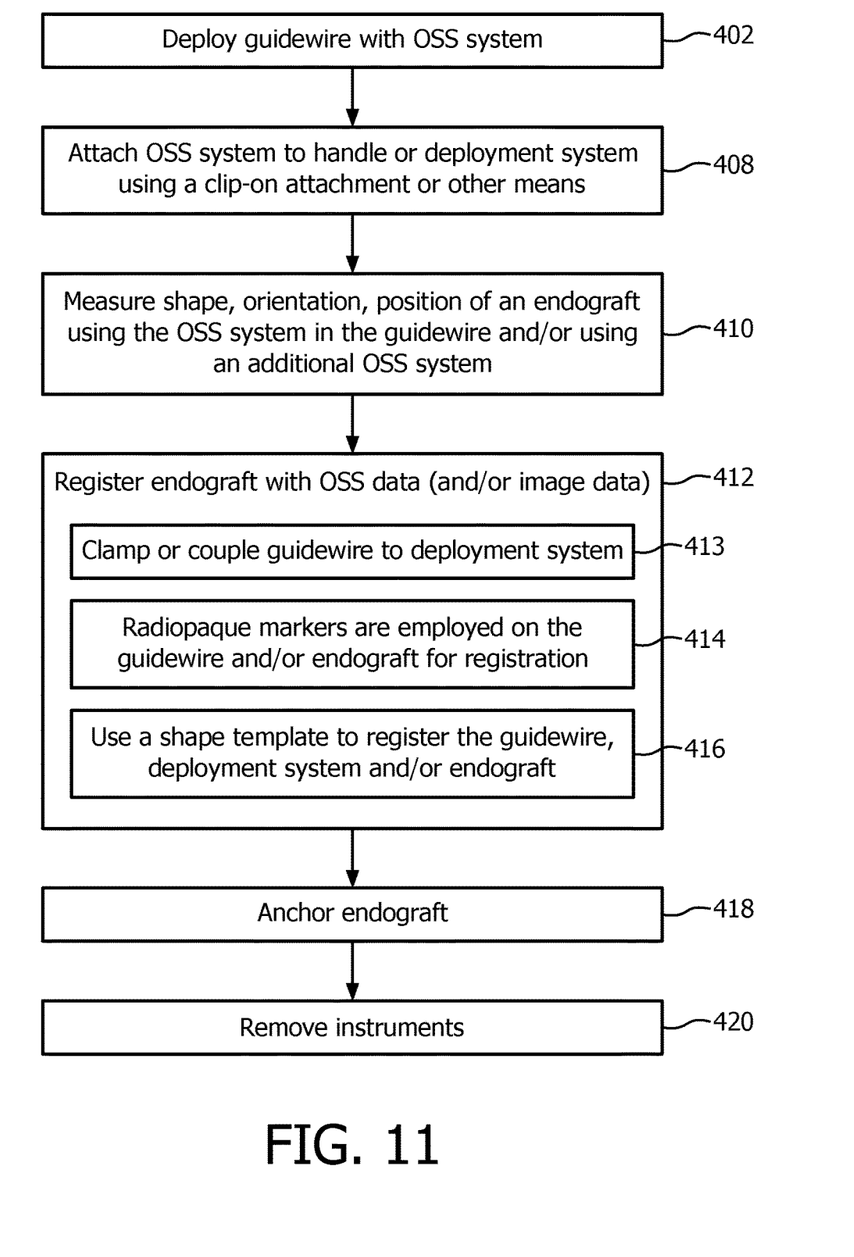
FIG. 11 is a flow diagram showing a method for endograft placement/deployment using an optical shape sensing system in a guidewire in accordance with illustrative embodiments.

Referring to FIG. 11, a method for endograft deployment is described and shown in accordance with illustrative embodiments. In block 402, a guide wire having an optical shape sensing (OSS) system within a lumen of the guide wire is deployed. The guide wire is configured to deliver an endograft into a vessel. The guide wire may be disposed within a deployment system or tool. The deployment system or tool may have relative motion (e.g., free rotation, measured rotation, etc.) with respect to the guidewire or the relative motion may be constrained. The deployment system and the guidewire may be clamped together or coupled together when engaging at a particular point, etc.

In block 408, the OSS system may be attached to the at least one handle or deployment system using a clip-on attachment device or other means. In one embodiment, the deployment system may include two handles and the OSS system may be attached between the two handles to measure relative distance between the handles using the OSS system.

In block 410, shape, position and/or orientation of the guide wire are measured using the OSS system to identify a shape, position and orientation of the endograft during deployment. The shape, position and/or orientation of the handle may be measured with the OSS system inside the guide wire or may be measured using an additional OSS system.

In block 412, the endograft is registered with OSS data and/or with image data of the vessel where the endograft is placed. In block 413, the guidewire may be clamped or coupled to the deployment system to prevent relative motion therebetween. The deployment system may include at least one handle. The OSS system may also be coupled to the at least one handle. In block 414, the endograft is registered with the guide wire using one or more radiopaque markers along a length of the guidewire and/or on the endograft. In block 416, the guidewire may include a shape template and the OSS data is registered to the image data using the shape template. The shape template includes a distinctive shape that can be matched between OSS data and image data to register one or more of the deployment system, the guidewire, the stent, etc.

In block 418, the endograft is anchored in the blood vessel. In block 420, the guidewire and the OSS system are removed from the vessel.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function; and
 e) no specific sequence of acts is intended to be required unless specifically indicated.

Having described preferred embodiments for device visualization through optical shape sensing of a guidewire (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical device deployment system, comprising:
   a main body;
   a guidewire capable of being passed through the main body and including a lumen; and
   an optical shape sensing (OSS) system comprising an optical fiber, which comprises a fiber Bragg grating sensor, the OSS system being configured to pass through the lumen in the guidewire, the OSS system being configured to measure at least one of shape, position or orientation of a medical device being deployed relative to an anatomical feature and output optical shape sensing data obtained from reflections within the optical fiber of the OSS system indicative of a shape of the optical fiber, wherein: the guidewire is centrally located in the main body;
   the OSS system is centrally located in the lumen of the guidewire between two handles; and
   a processor configured to determine a relative distance between the handles using the OSS system.

2. The deployment system as recited in claim 1, wherein the guidewire is deformed with a shape template for registering the position in the optical shape sensing data along the guidewire.

3. The deployment system as recited in claim 1, further comprising at least one handle coupled to the main body, the at least one handle including an attachment position for the OSS system exiting the guidewire.

4. The deployment system as recited in claim 1, further comprising at least one handle coupled to the main body, the at least one handle including an attachment position for an additional OSS system.

5. The deployment system as recited in claim 1, further comprising a clamping mechanism configured to clamp the main body to the guidewire.

6. The deployment system as recited in claim 1, further comprising a first coupling feature on the main body and a second coupling feature on the guidewire, the first coupling feature and the second coupling feature being configured to engage each other to connect to prevent relative motion therebetween.

7. The deployment system as recited in claim 1, further comprising a rotation tracking sensor configured to measure rotation between the main body and the guidewire.

8. The deployment system as recited in claim 1, further comprising an endograft; and radiopaque markers disposed on the guidewire to permit registration between the guidewire and the endograft.

9. The deployment system as recited in claim 1, further comprising at least one clip-on attachment configured to attach the OSS system to a control handle of the deployment system, wherein the at least one clip-on attachment includes an adhesive portion coupled to the deployment system to attach the OSS system, the adhesive portion including a radiopaque feature.

10. The deployment system as recited in claim 1, wherein the deployment system is an endograft deployment system or is a deployment system which includes a mitral clip, a valve or a balloon catheter.

11. An endograft deployment system, comprising:
    a workstation including a processor;
    a tangible, non-transitory computer readable medium that stores executable instructions, which when executed by the processor, cause the processor to: interpret optical shape sensing data; and register the optical shape sensing data to pre-operative or intra-operative images;
    a deployment system including a tube;
    a guidewire capable of being passed through the tube, the guidewire including a lumen;
    an optical shape sensing (OSS) system comprising an optical fiber, which comprises a fiber Bragg grating sensor, the OSS system being configured to pass through the lumen in the guidewire, and configured to measure at least one of shape, position or orientation of an endograft relative to a blood vessel for placement of the endograft to provide the optical shape sensing data wherein:
    the guidewire is centrally located in the tube; and the OSS system is centrally located in the lumen of the guidewire; the OSS system is attached between two handles; and the executable instructions further cause a processor to determine a relative distance between the handles using the OSS system.

12. The endograft deployment system as recited in claim 11, wherein the guidewire is deformed with a shape template for registering the position in shape data along the guidewire.

13. The endograft deployment system as recited in claim 11, further comprising at least one handle coupled to the tube, the at least one handle including an attachment position for the OSS system exiting the guidewire.

14. The endograft deployment system as recited in claim 11, further comprising at least one handle coupled to the tube, the at least one handle including an attachment position for an additional OSS system.

15. The endograft deployment system as recited in claim 11, further comprising:
    a clamping mechanism configured to clamp the tube to the guidewire;
    a first coupling feature on the tube and a second coupling feature on the guidewire, the first coupling feature and the second coupling feature being configured to engage each other to connect to prevent relative motion therebetween;
    a rotation tracking sensor configured to measure rotation between the tube and the guidewire;
    radiopaque markers disposed on the guidewire to permit registration between the guidewire and the endograft; and
    at least one clip-on attachment configured to attach the OSS system to a control handle of the deployment system,
    wherein the at least one clip-on attachment includes an adhesive portion coupled to the deployment system to attach the OSS system, the adhesive portion including a radiopaque feature.

16. A method for endograft deployment, comprising:
    deploying a guidewire having an optical shape sensing (OSS) system within a lumen of a guide wire, the guide wire configured to deliver an endograft into a vessel, wherein: the guidewire is centrally located in a tube; and the OSS system is centrally located in the lumen of the guidewire;
    measuring at least one of shape, position or orientation of the guide wire using the OSS system to identify a shape, position or orientation of the endograft during deployment;
    registering OSS data with image data on the vessel where the endograft is placed;
    anchoring the endograft in a blood vessel;
    removing the guidewire and the OSS system from the vessel;

attaching the OSS system between two handles; and
determining a relative distance between the handles with a processor.

17. The method as recited in claim 16, wherein deploying includes using a deployment system having at least one handle, the OSS system being coupled to the at least one handle and the method further comprises:
measuring the at least one of shape, position or orientation of the handle along with the guide wire.

18. The method as recited in claim 16, further comprising attaching the OSS system to at least one handle using a clip-on attachment device.

19. The method as recited in claim 16, wherein registering OSS data with image data on the vessel includes registering the endograft with the guidewire using one or more radiopaque markers along a length of the guidewire.

20. The method as recited in claim 16, wherein the guidewire is deformed by a shape template and the step of registering includes registering the OSS data to the image data using the shape template.

\* \* \* \* \*